(12) United States Patent
Burket et al.

(10) Patent No.: US 8,524,924 B2
(45) Date of Patent: Sep. 3, 2013

(54) PROCESS FOR FURFURAL PRODUCTION FROM BIOMASS

(75) Inventors: Christopher Burket, Wilmington, DE (US); Subramaniam Sabesan, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 269 days.

(21) Appl. No.: 12/973,980

(22) Filed: Dec. 21, 2010

(65) Prior Publication Data

US 2012/0157697 A1 Jun. 21, 2012

(51) Int. Cl.
*C07D 307/50* (2006.01)
*C07D 307/42* (2006.01)

(52) U.S. Cl.
USPC ........................................ 549/489; 549/488

(58) Field of Classification Search
USPC ....................................................... 549/489
See application file for complete search history.

(56) References Cited

U.S. PATENT DOCUMENTS

| | | | |
|---|---|---|---|
| 2,750,394 | A | 6/1956 | Peniston |
| 4,154,744 | A | 5/1979 | Hamada et al. |
| 4,533,743 | A | 8/1985 | Medeiros et al. |
| 6,441,202 | B1 | 8/2002 | Lightner |
| 7,572,925 | B2 | 8/2009 | Dumesic et al. |
| 2003/0032819 | A1 | 2/2003 | Lightner |
| 2008/0033188 | A1 | 2/2008 | Dumesic et al. |
| 2009/0124839 | A1 | 5/2009 | Dumesic et al. |
| 2010/0004437 | A1 | 1/2010 | Binder et al. |

FOREIGN PATENT DOCUMENTS

WO WO2007146636 A1 12/2007

OTHER PUBLICATIONS

Croker et al, Ind. Eng. Chem. Fundamentals, vol. 23, p. 480-484 (1984).*
Moreau et al, Industrial Crops Products, vol. 7, p. 95-99 (1998).*
Amiri et al., Production of furans from rice straw by single-phase and biphasic systems, Carbohydrate Research, 2010, 2133-2138, vol. 345.
Weingarten et al., Kinetics of furfural production by dehydration of xylose in a biphasic reactor with microwave heating, Green Chemistry, The Royal Society of Chemistry, 2010, 1423-1429, vol. 12.
Zhao et al., Metal Chlorides in Ionic Liquid Solvents Convert Sugars to 5-Hydroxymethylfurfural, Science, 2007, 1597-1600, vol. 316.
Dias et al., Dehydration of xylose into furfural over micro-mesoporous sulfonic acid catalysts, Journal of Catalysis, 2005, 414-423, vol. 229.
Chheda et al., Production of 5-hydroxymethylfurfural and furfural by dehydration of biomass-derived mono- and poly-saccharides, Green Chemistry, The Royal Society of Chemistry, 2007, 342-350, vol. 9.
Mamman et al., Furfural: Hemicellulose/xylose-derived biochemical; Biofuels Bioproducts & Biorefining, 2008, 438-454, vol. 2.
Vazquez et al., Hydrolysis of sorghum straw using phosphoric acid: Evaluation of furfural production, Bioresource Technology, 2007, 3053-3060, vol. 98.
International Search Report, PCT International Application No. PCT/US2011/066332, Mailed Nov. 30, 2013.

* cited by examiner

*Primary Examiner* — Bernard Dentz

(57) ABSTRACT

Furfural is produced from a lignocellulosic feedstock comprising glucan and xylan. The feedstock is contacted with water in the presence of an acid catalyst. The resulting mixture is contacted with at least one water-immiscible organic solvent to form a mixture comprising an aqueous phase and an organic phase. Under suitable reaction conditions, furfural is produced and preferentially partitions into the organic phase, from which it may be recovered.

14 Claims, No Drawings

PROCESS FOR FURFURAL PRODUCTION FROM BIOMASS

FIELD OF THE INVENTION

Methods for the production of furfural from biomass are provided. Specifically, methods for obtaining furfural selectively in good purity from lignocellulosic biomass under biphasic conditions are provided.

BACKGROUND

Furfural is an industrially useful chemical. Conventionally, furfural can be produced from $C_5$ sugars which have been obtained from hydrolysis of the hemicellulose contained in biomass. Typically, the hydrolysis of biomass is performed with aqueous acids at relatively high temperatures to obtain $C_5$ and $C_6$ sugars derived from xylan and glucan, respectively. Any furfural generated, when left in the monophasic aqueous reaction mixture of sugars, can undergo degradation via condensation initiated by reactive sugar intermediates. Besides resulting in lower yield of the desired furfural product, costly separation steps to isolate the furfural from other intermediates is needed. Such separation step(s) can increase process complexity as well.

U.S. Pat. No. 4,154,744 relates to an improved process for producing a furan derivative having the formula shown below

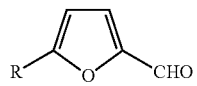

wherein R is hydrogen, methyl, or chloromethyl, which comprises reacting a monosaccharide or a disaccharide with hydrochloric acid in a mixture containing water, an organic solvent and a catalytic amount of a surface active agent.

U.S. Pat. No. 4,533,743 discloses that furfural yield and selectivity are maximized by reacting a 1 to 10 percent pentose 0.05 to 0.2 normal mineral acid aqueous solution in a plug flow reactor operated at a temperature between 220° C. and 300° C. Two preferred arrangements are disclosed: a single phase, pentose recycle operation in which the furfural is recovered by solvent extraction and distillation, and a two phase, solvent recycle operation in which solvent is added to the reactor and furfural is recovered from the solvent by distillation.

United States Patent Application Publication No. 2008/0033188 relates to a process to make furan derivative compounds. The process comprises dehydrating a carbohydrate feedstock solution, optionally in the presence of an acid catalyst, in a reaction vessel containing a biphasic reaction medium comprising an aqueous reaction solution and a substantially immiscible organic extraction solution. The aqueous reaction solution, the organic extraction solution, or both the aqueous reaction solution and the organic extraction solution, contain at least one modifier to improve selectivity of the process to yield furan derivative compounds in general, and 5-hydroxymethyl-2-furfural (HMF) in particular.

Processes for obtaining furfural in high purity and selectivity from biomass continue to be sought. In particular, processes are desired in which lignocellulosic biomass comprising both glucan and xylan can be used as feedstock to provide furfural selectively and in good purity, relatively free of HMF. Also desired are processes in which the separation of furfural from HMF is simplified.

SUMMARY

Described herein are processes for the production and separation of furfural from lignocellulosic biomass. The described processes involve contacting the biomass, in the presence of an acid catalyst and under suitable conditions, with water and at least one water-immiscible organic solvent as described herein. The reaction conditions are selected to favor conversion of the xylan component of the biomass feedstock to furfural, and the at least one water-immiscible organic solvent is chosen to preferentially partition the furfural into the organic phase.

In one embodiment, a process for the production of furfural is described, the process comprising the steps of:
a) providing a lignocellulosic feedstock comprising glucan and xylan;
b) contacting the feedstock with water in the presence of an acid catalyst to form a mixture;
c) contacting the mixture formed in step b) with at least one water-immiscible organic solvent comprising at least one aliphatic hydrocarbon, cycloalkane, aromatic hydrocarbon, polyether containing ester or ether end groups, plant-derived oil, or mixtures thereof under suitable reaction conditions to form a mixture comprising an aqueous phase and a furfural-containing organic phase; and
d) optionally, recovering furfural from the organic phase.

DETAILED DESCRIPTION OF THE INVENTION

Definitions

The methods described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" refers to a composition comprising both lignin and hemicellulose. Lignocellulosic material may also comprise cellulose.

As used herein, the term "water-immiscible" refers to a solvent or solvent mixture which is incapable of mixing with water or an aqueous solution to form one liquid phase.

As used herein the term "partition coefficient", abbreviated herein as $K_p$, means the ratio of the concentration of a compound in the two liquid phases of a mixture of two immiscible solvents at equilibrium. A partition coefficient is a measure of the differential solubility of a compound between two immiscible solvents. As used herein, the term "partition coefficient for furfural" refers to the ratio of concentrations of furfural between the organic phase comprising the organic solvent or solvent mixture and the water or aqueous phase. Partition coefficient, as used herein, is synonymous with the term "distribution coefficient."

As used herein, the term "fatty acid" refers to a monocarboxylic acid with an unbranched aliphatic tail, or chain. Fatty acids are derived from, or contained in esterified form in, an animal or vegetable fat, oil, or wax. Natural fatty acids commonly have a chain of 4 to 28 carbon atoms. Fatty acids can be bound to other molecules, such as in triglycerides.

As used herein, the term "free fatty acid" refers to fatty acids which are not bound to other molecules. A free fatty acid is obtained, for example, when a triglyceride is broken down into its components (fatty acids and glycerol).

As used herein, the term "triglyceride" refers to a glyceride formed by esterification of a glycerol molecule with three fatty acids. The three fatty acids can be all different, all the same, or only two the same. Triglycerides are the main constituent of vegetable oil and animal fats.

In the processes described herein, a lignocellulosic feedstock comprising glucan and xylan is contacted with water in the presence of an acid catalyst, then with at least one water-immiscible organic solvent as described herein under suitable reaction conditions to form a mixture comprising an aqueous phase and a furfural-containing organic phase. Optionally, the processes further comprise recovering furfural from the organic phase. One of the economical advantages of the processes is that no modifiers are used in the aqueous or organic phases, and thus no modifiers need to be separated from the furfural or any process streams.

The source of the lignocellulosic feedstock is not determinative of the invention, and the biomass may be from any source. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment of the invention, biomass that is useful includes corn cobs, wheat straw, sawdust, and sugar cane bagasse.

The lignocellulosic feedstock may be used directly as obtained from the source, or energy may be applied to the biomass to reduce the size, increase the exposed surface area, and/or increase the availability of lignin, cellulose, hemicellulose, and/or oligosaccharides present in the biomass to the acid catalyst, to the water, and to the water-immiscible organic solvent used in the contacting step(s). Energy means useful for reducing the size, increasing the exposed surface area, and/or increasing the availability of lignin, cellulose, hemicellulose, and/or oligosaccharides present in the lignocellulosic feedstock include, but are not limited to, milling, crushing, grinding, shredding, chopping, disc refining, ultrasound, and microwave. This application of energy may occur before and/or during contacting with the water and/or immiscible organic solvent. The lignocellulosic feedstock may be used directly as obtained from the source or may be dried to reduce the amount of moisture contained therein.

The lignocellulosic feedstock is contacted with water in the presence of an acid catalyst. In one embodiment, an amount of water is used which is at least equivalent to that of the lignocellulosic feedstock on a weight basis. Typically, the use of more water provides a more dilute solution of xylose (from hydrolysis of the xylan contained in the lignocellulosic biomass), which enables a higher overall yield of furfural to be realized. However, minimizing the amount of water used generally improves process economics by reducing process volumes. In practical terms, the amount of water used relative to the lignocellulosic feedstock will depend on the moisture content of the feedstock and on the desired yield of furfural, as well as the ability to provide sufficient mixing, or intimate contact, for the biomass hydrolysis and furfural production reactions to occur at a practical rate.

The acid catalyst comprises a mineral acid, a heteropolyacid, an organic acid, or a combination thereof. In one embodiment, the acid catalyst is a mineral acid comprising sulfuric acid, phosphoric acid, hydrochloric acid, or a combination of these. In one embodiment, the acid catalyst is a heteropolyacid comprising phosphotungstic acid, molybdophosphoric acid, or a combination of these. In one embodiment, the acid catalyst is an organic acid comprising oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination of these. An example of a suitable alkyl sulfonic acid is methane sulfonic acid. An example of a suitable aryl sulfonic acid is toluenesulfonic acid. An example of a suitable halogenated acetic acid is trifluoroacetic acid. An example of a suitable halogenated alkylsulfonic acid is trifluoromethane sulfonic acid. An example of a suitable halogenated aryl sulfonic acid is fluorobenzenesulfonic acid.

The acid catalyst catalyzes hydrolysis of the xylan and glucan contained in the biomass to monomeric sugars, and also the conversion of xylose to furfural and glucose to hydroxymethylfurfural. The concentration of the acid catalyst in the aqueous solution is selected to provide acceptable rates of xylan conversion to furfural (through the combination of xylan hydrolysis and xylose dehydration) while minimizing unwanted side reactions. In one embodiment, the acid catalyst may be combined with at least a portion of the water and contacted with the lignocellulosic feedstock as an aqueous solution. The acid catalyst may be obtained from commercial sources or prepared according to known methods.

Organic solvents useful in the methods described herein are water-immiscible. A suitable organic solvent or solvent mixture should meet the criteria for an ideal solvent for two liquid phase production or recovery of furfural. Specifically, the organic solvent composition should (i) be substantially immiscible with water or the aqueous phase, (ii) have a high partition coefficient ($K_P$) for the extraction of furfural, (iii) have a low partition coefficient for the extraction of 5-hydroxymethylfurfural, and (iv) have a low tendency to form emulsions with water or the aqueous phase. In addition, for improved process operability and economics, the organic solvent should have a boiling point suitable for downstream separation of the solvent and the furfural. The boiling point can affect the cost and method of furfural recovery. For example, in the case where the furfural is recovered from the organic phase by distillation, the boiling point of the organic solvent should be sufficiently higher or lower than the boiling point of furfural so as to enable facile distillation of the furfural from the solvent or distillation of the solvent from furfural.

Water-immiscible organic solvents useful in the methods described herein comprise at least one aliphatic hydrocarbon, cycloalkane, aromatic hydrocarbon, polyether containing ester or ether end groups, plant-derived oil, or mixtures thereof. As used herein, the term "mixtures thereof" encompasses both mixtures within and mixtures between the solvent classes, for example mixtures within aliphatic hydrocarbons, and also mixtures between aliphatic hydrocarbons and aromatic hydrocarbons, for example.

The at least one water-immiscible organic solvent may be one or more aliphatic hydrocarbons, for example an aliphatic hydrocarbon having from 3 to about 12 carbon atoms, or from 3 to about 8 carbon atoms, for example. The aliphatic hydrocarbon may be linear or branched. Optionally, the aliphatic hydrocarbon may be substituted, for example with at least one halogen atom. In one embodiment, the organic solvent is an aliphatic hydrocarbon comprising $CF_3CH_2CH_2CHF_2$, $CF_3CF_2CFHCFHCF_3$, $CF_3CF_2CHCl_2$, or mixtures thereof.

The at least one water-immiscible organic solvent may be one or more cycloalkanes, for example a cycloalkane having from 6 to about 8 carbon atoms. The cycloalkane may be unsubstituted or substituted, for example with at least one halogen atom. In one embodiment, the organic solvent is a cycloalkane comprising cyclohexane, methylcyclohexane, or mixtures thereof.

The at least one water-immiscible organic solvent may be one or more aromatic hydrocarbons, for example an aromatic hydrocarbon having from 6 to about 8 carbon atoms. The aromatic hydrocarbon may be substituted, for example with alkyl, halogenated alkyl, or halogen substituents. In one embodiment, the organic solvent is an aromatic hydrocarbon comprising benzene, toluene, a xylene, trifluorotoluene, or mixtures thereof.

The at least one water-immiscible organic solvent may be a polyether of sufficient molecular weight to be immiscible in water and containing ester or ether end groups of one to six carbon atoms. Polyethers containing ester end groups may be obtained commercially or by reacting polyethers containing hydroxyl end groups with carboxylic acids under appropriate reaction conditions, for example by reacting polyethylene glycol with acetic anhydride and pyridine, a reaction method well known in the art. The ester end groups may be linear or branched and may include, for example, acetate, propionate, or butyrate groups. Polyethers containing ether end groups may be obtained commercially or by reacting polyethers containing hydroxyl end groups with alcohols under appropriate reaction conditions, for example by reacting polyethyleneglycol with benzyl iodide and sodium hydride, a methodology well known in the art (see for example, Theodora W. Greene, Peter. G. M. Wuts, *Protective Groups in Organic Synthesis*, Second Edition, John Wiley & Sons, Inc., New York 1991). The ether end groups may be linear or branched and may include, for example, methoxy, ethoxy, propoxy, or butoxy groups. The polyether may include polyethylene glycol or polypropylene glycol, for example. In one embodiment, the at least one water-immiscible organic solvent is a polyether comprising polyethylene glycol containing ester or ether end groups, polypropylene glycol containing ester or ether end groups, or mixtures thereof.

The at least one water-immiscible organic solvent may be at least one plant-derived oil. In one embodiment, the plant-derived oil may comprise one or more free fatty acids. For example, the plant-derived oil may comprise lauric acid, myristic acid, palmitic acid, or a combination of these. In one embodiment, the plant-derived oil may comprise one or more triglycerides, wherein the triglycerides are derived from a fatty acid.

In one embodiment, the plant-derived oil may comprise triglycerides derived from a plant selected from the group consisting of corn, pine, rape seed, canola, sunflower, jathropa, seashore mallow, and combinations of two or more thereof. Oil from genetically modified plant varieties may also be used, for example genetically modified high stearic acid or high lauric acid canola varieties. In one embodiment, the plant-derived oil may be a vegetable oil selected from the group consisting of corn oil, coconut oil, palm kernel oil, palm oil, soybean oil, and cottonseed oil, or mixtures thereof.

Table 1 shows the fatty acid chain lengths of several triglyceride and fatty acid sources by weight percent. The fatty acid chain lengths in Table 1 are given using lipid nomenclature of the form C:D, where C is the number of carbon atoms in the fatty acid and D is the number of double bonds in the fatty acid. For example, C18:1 refers to an 18 carbon chain with 1 unsaturated bond, C18:2 refers to an 18 carbon chain with 2 unsaturated bonds, and C18:3 refers to an 18 carbon chain with 3 unsaturated bonds. In Table 1, $C_{18+}$ refers to fatty acids containing greater than 18 carbons. The values in Table 1 are representative of the triglyceride content of the indicated oils, which can vary from sample to sample.

TABLE 1

Fatty Acid Chain Lengths of Triglyceride and Fatty Acid Sources (by weight percent).

|       | Coconut Oil | Palm Kernel Oil | Palm Oil | Soybean Oil |
|-------|-------------|-----------------|----------|-------------|
| C6:0  | 0.5         |                 |          |             |
| C8:0  | 7.5         | 3.5             |          |             |
| C10:0 | 5.8         | 3.4             |          |             |
| C12:0 | 45.6        | 46.2            |          |             |

TABLE 1-continued

Fatty Acid Chain Lengths of Triglyceride and
Fatty Acid Sources (by weight percent).

| | Coconut Oil | Palm Kernel Oil | Palm Oil | Soybean Oil |
|---|---|---|---|---|
| C14:0 | 18.4 | 17.0 | 1.0 | |
| C16:0 | 9.2 | 8.8 | 45.4 | 10.2 |
| C16:1 | | | | |
| C18:0 | 3.5 | 3.0 | 4.3 | 4.4 |
| C18:1 | 6.2 | 15.0 | 38.8 | 23.3 |
| C18:2 | 2.8 | 3.1 | 9.9 | 53.2 |
| C18:3 | | | | 6.5 |
| $C_{18+}$ Free Acids | 0.5 | | 0.6 | 2.4 |
| Total | 100.0 | 100.0 | 100.0 | 100.0 |

Refined corn oil is typically 99% triglyceride, with proportions of approximately 65% polyunsaturated fatty acid, 33% monounsaturated fatty acid, and 15% saturated fatty acid. Of the saturated fatty acids, 80% are palmitic acid (lipid number of C16:0), 14% stearic acid (C18:0), and 3% arachidic acid (C20:0). Over 99% of the monounsaturated fatty acids are oleic acid (C18:1 c). 98% of the polyunsaturated fatty acids are the omega-6 linoleic acid (C18:2 n-6 c,c) with the 2% remainder being the omega-3 alpha-linolenic acid (C18:3 n-3 c,c,c).

In one embodiment, the at least one water-immiscible organic solvent comprises toluene, trifluorotoluene, corn oil, or mixtures thereof.

The at least one water-immiscible organic solvent is typically available commercially from various sources, such as Sigma-Aldrich (St. Louis, Mo.), in various grades, many of which may be suitable for use in the processes disclosed herein. Technical grades of a solvent can contain a mixture of compounds, including the desired component and higher and lower molecular weight components or isomers.

The at least one water-immiscible organic solvent can be added with the water or after addition of the water to the lignocellulosic feedstock. In one embodiment, the step of contacting the feedstock with water in the presence of an acid catalyst [step (b) of the processes disclosed herein] is performed prior to the step of contacting the mixture formed in step (b) with at least one water-immiscible organic solvent to form a mixture comprising an aqueous phase and a furfural-containing organic phase [step (c) of the processes disclosed herein]. In one embodiment, steps (b) and (c) are performed concurrently.

The relative amounts of the water (or aqueous acidic solution) and the organic solvent can vary within a suitable range. In one embodiment, the volume ratio of water to organic solvent used to form a mixture comprising an aqueous phase and a furfural-containing organic phase is from about 95:5 to about 5:95. In one embodiment, the volume ratio of water to organic solvent is from about 10:1 to about 1:10. In one embodiment, the volume ratio of water to organic solvent is from about 5:1 to about 1:5. In one embodiment, the volume ratio of water to organic solvent is from about 2:1 to about 1:2. The optimal range reflects maximization of the extraction process, for example balancing a relatively high partition coefficient for furfural with an acceptable solvent cost or an acceptable boiling point. For the processes described herein for the production or recovery of furfural from a lignocellulosic feedstock, the temperature, contacting time, xylan content of the lignocellulosic feedstock, furfural concentrations in the aqueous and organic phases, relative amounts of organic solvent and water (or aqueous acidic solution), specific solvent(s) used, presence of other organic solutes, and presence of aqueous solutes are related; thus these variables may be adjusted as necessary within appropriate limits to optimize the process as described herein.

In the methods described herein, the ratio of solid biomass to the sum of the aqueous acidic solution and the organic solvent may be from about 1:1 to about 1:250 on a weight basis. When expressed as a percentage, the solids loading may typically be from about 50% to about 0.4%, for example from about 25% to about 5%. Useful ranges of solids loading are dependent on the viscosity of the lignocellulosic feedstock in combination with the acid catalyst, water, and water-immiscible organic solvent, and may be affected by the type of biomass used and the particle size, for example. The biomass concentration may be maximized to the extent possible to minimize the volume of the contacting vessel and to make the process more economical. From a practical viewpoint, high ratios of the weight of biomass to the weight of water+ water-immiscible solvent may be limited by the ability to provide sufficient mixing, or intimate contact, for contacting to occur at a practical rate.

Suitable reaction conditions to form a mixture comprising an aqueous phase and a furfural-containing organic phase include a temperature of about 100° C. to about 220° C., for example from about 120° C. to about 160° C.

The contacting of the lignocellulosic feedstock with water and at least one water-immiscible organic solvent may be carried out for a period of time ranging from about 10 seconds to about 30 hours, for example from 5 minutes to about 15 hours. Typically, the contacting may be from 1 hour to about 5 hours.

The contacting of the lignocellulosic feedstock with water and at least one water-immiscible organic solvent may be performed at a relatively high temperature for a relatively short period of time, for example at about 140° C. to about 220° C. for about 180 minutes to about 10 minutes.

For contacting of the lignocellulosic feedstock with water and at least one water-immiscible organic solvent, the temperature, contacting time, acid, acid concentration, amount of water, ratio of water to organic solvent, the biomass concentration, the biomass type, the amount of lignin present, and the biomass particle size are related; thus, these variables may be adjusted as necessary to produce a two-phase mixture comprising an aqueous phase and a furfural-containing organic phase at a sufficient rate and in a practical manner.

The contacting of the lignocellulosic feedstock with water and at least one water-immiscible organic solvent may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, N. C. (in Perry, R. H. and Chilton, C. H. (eds), Chemical Engineer's Handbook, 5$^{th}$ Edition (1973) Chapter 4, McGraw-Hill, N.Y.). The contacting step may be carried out as a batch process, or as a continuous process. In one embodiment, contacting the lignocellulosic feedstock with at least one water-immiscible organic solvent may be performed in the same vessel as the contacting with water and an acid catalyst. In one embodiment, contacting the lignocellulosic feedstock with water in the presence of an acid catalyst may be performed in one vessel, and the resultant mixture transferred to another vessel for contacting with at least one water-immiscible organic solvent.

Contacting the lignocellulosic feedstock with water and a water-immiscible organic solvent under suitable reaction conditions as described herein above provides a mixture comprising an aqueous phase and an organic phase. Residual biomass can be present as an additional, solid phase. Furfural (FF) preferentially partitions into the organic phase, decreasing the concentration of furfural in the aqueous phase. Appropriate choices of organic solvent and contacting conditions enable compounds such as hydroxymethylfurfural to partition preferentially into the aqueous phase, which provides furfural in good purity, relatively free of HMF, in the organic phase. In one embodiment, the organic phase further comprises HMF, and the ratio of FF:HMF in the organic phase is at least 10:1 on a weight basis. In one embodiment, the ratio of FF:HMF in the organic phase is at least 12:1 on a weight basis. Such ratios of FF to HMF in the organic phase, or higher, are desirable as the furfural can be recovered from the organic phase selectively and in good purity.

The furfural-containing organic phase can be separated from the aqueous phase using methods known in the art, including but not limited to, siphoning, decantation, centrifugation, using a gravity settler, membrane-assisted phase splitting, and the like. Recovery of the furfural from the furfural-containing organic phase can be done using methods known in the art, including but not limited to, distillation, adsorption by resins, separation by molecular sieves, pervaporation, and the like. In one embodiment, distillation may be used to recover the furfural from the furfural-containing organic phase. The organic solvent may be recycled to contact additional lignocellulosic feedstock.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. Sulfuric acid, cyclohexane, trifluorotoluene, and methyl isobutyl ketone (MIBK) were obtained from Sigma-Aldrich (St. Louis, Mo.). Toluene was supplied by EMD (Darmstadt, Germany). Corn oil was purchased from a local grocery. Calcium carbonate was obtained from Fisher Scientific (Fair Lawn, N.J.). Distilled water was utilized in all examples.

Corn cob particles (+10/−14 mesh) were purchased from Independence Corn Byproducts Co. (Independence, Iowa). Wheat straw and sugarcane bagasse were obtained from the National Institute of Standards & Technology (Gaithersburg, Md.). Both were −20/+74 mesh. Poplar sawdust was collected from a local sawmill. All biomass feedstocks were used as received.

The carbohydrate composition of the biomasses was determined according to the NREL method NREL/TP-510-42618. The moisture content of the corn cob and poplar sawdust was determined by weighing the biomass before and after drying in a vacuum oven overnight at 120° C. The moisture content of the bagasse and wheat straw was measured according to NREL/TP-510-42621. The initial carbohydrate compositions of the feedstocks are reported in Table 2. The xylan content is reported as the sum of the xylan and arabinan components. Xylose concentrations are reported as the sum of xylose and arabinose.

TABLE 2

Carbohydrate Composition of Lignocellulosic Biomass Feedstocks Used

| Biomass | Moisture (wt %) | Xylan (wt %) | Glucan (wt %) |
|---|---|---|---|
| Corn Cob | 7.9 | 34.0 | 36.6 |
| Wheat Straw | 7.0 | 24.2 | 37.6 |
| Bagasse | 6.0 | 23.3 | 40.2 |
| Poplar Sawdust | 40.2 | 18.1 | 40.7 |

The following abbreviations are used: "C" is Celsius, "mm" is millimeter(s), "μm" is micrometer(s), "μL" is microliter(s), "mL" is milliliter(s), "min" is minute(s), "g" is gram(s), "wt" is weight, "wt %" means weight percent, "RPM" is revolutions per minute, "GC" is gas chromatography, "HPLC" is high pressure liquid chromatography, "FF" is furfural, "HMF" is hydroxymethylfurfural, "Comp." is Comparative Example.

General Procedure for Examples 1-10

Preparation of furfural from biomass in biphasic (liquid/liquid) conditions was conducted in batch mode using the procedure described here. Batch reactions were performed in a 300 mL mini bench top autoclave reactor (model 4561, Parr Instrument Co., Moline, Ill.) with all internal wetted parts constructed from ZR705. External fittings were constructed with 316 stainless steel. Heat was supplied by an external electrical mantle. The reaction mixture was stirred at 300 RPM. In a typical experiment an aqueous solution containing the mineral acid (3.75 wt % sulfuric acid) was added to the biomass in a 100 mL beaker. The resulting mixture was thoroughly mixed with a spatula and transferred to the reactor. The specified amount of organic solvent was added and the reactor was sealed and purged with nitrogen prior to heating. At the conclusion of the reaction the vessel was submerged in an ice bath to rapidly quench the mixture to room temperature (<25° C.). The contents of the reactor were transferred to a glass bottle and the organic and aqueous phases were allowed to separate.

Samples of the aqueous and organic phases were collected and passed through a 0.2 μm syringe filter prior to analysis. The aqueous phase was neutralized with calcium carbonate and re-filtered before it was analyzed by high pressure liquid chromatography (HPLC). The HPLC instrument employed was a HP 1100 Series equipped with Agilent 1200 Series refractive index (RI) detector and an auto injector (Santa Clara, Calif.). The analytical method was adapted from an NREL procedure (NREL/TP-510-42623). Separation and quantitation of monomeric sugars (glucose, xylose, and arabinose), furfural (FF), and hydroxymethylfurfural (HMF) in the aqueous layer—was performed by injecting the aqueous sample (10 μL) on to a Bio-Rad HPX-87P (Bio-Rad, Hercules, Calif.) column maintained at 85° C. Water was used as the eluant, with a flowrate of 0.6 mL/min. The reaction products in the eluant were identified with the RI detector operating at 55° C. Products in the organic layer were analyzed by gas chromatography (GC) using a HP 5890 GC instrument (Santa Clara, Calif.). The GC column was a 30 M DB-17 capillary with 0.320 mm I.D. and a 0.25 μm film thickness. Typically, 1 μL of organic solution was injected into the GC instrument. The injector and the detector temperature were set at 250° C. An internal standard of phenol in ethyl acetate was added to the samples in order to quantify the amounts of FF and HMF in the sample.

Furfural and hydroxymethylfurfural yields are based on the respective glucan and xylan plus arabinan compositions in the unreacted lignocellulosic biomass.

For the Comparative Examples and Examples 1-8 and 10, the mass of biomass added to the reactor was selected to maintain a maximum xylose concentration in the aqueous phase of less than 6 wt %.

Table 3 summarizes the reaction conditions and product yields for the Comparative Examples and Examples 1-10.

Comparative Example A

Corn Cob Contacted Only with Aqueous Acid

A suspension of corn cob (32.9 g) in aqueous sulfuric acid (200.0 g, 3.75 wt %) was heated in the reactor to 150° C. for 78 min. The reaction mixture was processed and analyzed as described above but with no addition of organic solvent and no formation of a mixture comprising an aqueous phase and an organic phase. The yield of furfural was 23% and that of HMF was 1%.

Comparative Example B

Corn Cob Contacted with Aqueous Acid and a Non-Selective Solvent

A suspension of corn cob (3.5 g) in aqueous sulfuric acid (20.3 g, 3.75 wt %) and MIBK (141.4 g) was heated in the reactor to 150° C. for 75 min. The reaction mixture was processed and analyzed as described above. The yield of FF was 61% and that of HMF was 23%. The ratio of FF to HMF in the organic phase was 2:1 by weight.

Example 1

Corn Cob Contacted with Aqueous Acid and Toluene (Short Contact Time)

A suspension of corn cob (3.3 g) in aqueous sulfuric acid (20.0 g, 3.75 wt %) and toluene (167.1 g) was heated in the reactor to 150° C. for 79 min. The reaction mixture was processed and analyzed as described above. The yield of FF was 72% and that of HMF was 6%. The ratio of FF to HMF in the organic phase was 24:1 by weight.

Example 2

Corn Cob Contacted with Aqueous Acid and Toluene (Long Contact Time)

A suspension of corn cob (3.1 g) in aqueous sulfuric acid (20.1 g, 3.75 wt %) and toluene (174.2 g) was heated in the reactor to 150° C. for 180 min. The reaction mixture was processed and analyzed as described above. The yield of FF was 67% and that of HMF was 3%. The ratio of FF to HMF in the organic phase was 42:1 by weight.

Example 3

Corn Cob Contacted with Aqueous Acid and Trifluorotoluene

A suspension of corn cob (3.3 g) in aqueous sulfuric acid (19.9 g, 3.75 wt %) and trifluorotoluene (234.9 g) was heated in the reactor to 150° C. for 74 min. The reaction mixture was processed and analyzed as described above. The yield of FF was 69% and that of HMF was 7%. The ratio of FF to HMF in the organic phase was 25:1 by weight.

Example 4

Corn Cob Contacted with Aqueous Acid and Cyclohexane

A suspension of corn cob (2.9 g) in aqueous sulfuric acid (20.1 g, 3.75 wt %) and cyclohexane (150.4 g) was heated in the reactor to 150° C. for 79 min. The reaction mixture was processed and analyzed as described above. The yield of FF was 62% and that of HMF was 2%. HMF was not detected in the organic phase.

Example 5

Wheat Straw Contacted with Aqueous Acid and Toluene

A suspension of wheat straw (5.0 g) in aqueous sulfuric acid (20.2 g, 3.75 wt %) and toluene (150.4 g) was heated in the reactor to 150° C. for 79 min. The reaction mixture was processed and analyzed as described above. The yield of FF was 66% and that of HMF was 2%. The ratio of FF to HMF in the organic phase was 27:1 by weight.

Example 6

Bagasse Contacted with Aqueous Acid and Toluene

A suspension of bagasse (4.9 g) in aqueous sulfuric acid (20.1 g, 3.75 wt %) and toluene (177.0 g) was heated in the reactor to 150° C. for 75 min. The reaction mixture was processed and analyzed as described above. The yield of FF was 72% and that of HMF was 5%. The ratio of FF to HMF in the organic phase was 29:1 by weight.

Example 7

Poplar Sawdust Contacted with Aqueous Acid and Toluene

A suspension of poplar sawdust (9.8 g) in aqueous sulfuric acid (20.0 g, 3.75 wt %) and toluene (163.6 g) was heated in the reactor to 150° C. for 75 min. The reaction mixture was processed and analyzed as described above. The yield of FF was 57% and that of HMF was 2%. HMF was not detected in the organic phase.

Example 8

Corn Cob Contacted with Aqueous Acid and Toluene (Low Xylose Concentration)

In this Example, the mass of biomass added to the reactor was selected to maintain a maximum xylose concentration in the aqueous phase of less than 0.5 wt %. A suspension of corn cob (0.3 g) in aqueous sulfuric acid (22.3 g, 3.75 wt %) and toluene (165.5 g) was heated in the reactor to 150° C. for 100 min. The reaction mixture was processed and analyzed as described above. The yield of FF was 91% and that of HMF was 2%. HMF was not detected in the organic phase.

Examples 9A, 9B, and 9C

Corn Cob Contacted with Aqueous Acid and Toluene (High Xylose Concentration)

A series of three experiments were performed to vary the reaction time at 150° C. The mass of biomass added to the reactor was selected to maintain a maximum xylose concentration in the aqueous phase of less than 36 wt %. Toluene was used as the organic phase. Results are presented in Table 3.

9A: A suspension of corn cob (6.0 g) in aqueous sulfuric acid (6.2 g, 3.75 wt %) and toluene (170.6 g) was heated in the reactor to 150° C. for 45 min. The reaction mixture was processed and analyzed as described above. The yield of FF was 68% and that of HMF was 8%. The ratio of FF to HMF in the organic phase was 16:1 by weight.

9B: A suspension of corn cob (6.0 g) in aqueous sulfuric acid (5.9 g, 3.75 wt %) and toluene (169.4 g) was heated in the reactor to 150° C. for 76 min. The reaction mixture was processed and analyzed as described above. The yield of FF was 69% and that of HMF was 13%. The ratio of FF to HMF in the organic phase was 12:1 by weight.

9C: A suspension of corn cob (5.3 g) in aqueous sulfuric acid (5.4 g, 3.75 wt %) and toluene (167.0 g) was heated in the reactor to 150° C. for 144 min. The reaction mixture was processed and analyzed as described above. The yield of FF was 69% and that of HMF was 13%. The ratio of FF to HMF in the organic phase was 15:1 by weight.

Example 10

Corn Cob Contacted with Aqueous Acid and Corn Oil

A suspension of corn cob (3.5 g) in aqueous sulfuric acid (20.2 g, 3.75 wt %) and corn oil (170.3 g) was heated in the reactor to 150° C. for 75 min. The reaction mixture was processed and analyzed as described above. The yield of FF was 56% and that of HMF was 2%. The ratio of FF to HMF in the organic phase was 43:1 by weight.

TABLE 3

Reactant Loading and Product Yield for Comparative Examples A and B and Examples 1-10

| Example | Biomass | Organic Solvent | Contact Time [min] | Sulfuric Acid Solution [g] | Biomass [g] | Organic [g] | Yields | |
|---|---|---|---|---|---|---|---|---|
| | | | | | | | FF ORG [%] | FF AQ [%] |
| Comp A | Corn Cob | None | 78 | 200.0 | 32.9 | 0.0 | 0 | 23 |
| Comp B | Corn Cob | MIBK | 75 | 20.3 | 3.5 | 141.4 | 60 | 1 |
| 1 | Corn Cob | Toluene | 79 | 20.0 | 3.3 | 167.1 | 70 | 2 |
| 2 | Corn Cob | Toluene | 180 | 20.1 | 3.1 | 174.2 | 66 | 2 |
| 3 | Corn Cob | Trifluorotoluene | 74 | 19.9 | 3.3 | 234.9 | 67 | 2 |
| 4 | Corn Cob | Cyclohexane | 79 | 20.1 | 2.9 | 150.4 | 48 | 14 |
| 5 | Wheat Straw | Toluene | 75 | 20.2 | 5.0 | 173.6 | 64 | 2 |
| 6 | Bagasse | Toluene | 75 | 20.1 | 4.9 | 177.0 | 70 | 2 |
| 7 | Poplar Sawdust | Toluene | 75 | 20.0 | 9.8 | 163.6 | 56 | 2 |
| 8 | Corn Cob | Toluene | 100 | 22.3 | 0.3 | 165.5 | 89 | 2 |
| 9A | Corn Cob | Toluene | 45 | 6.2 | 6.0 | 170.6 | 68 | 1 |
| 9B | Corn Cob | Toluene | 76 | 5.9 | 6.0 | 169.4 | 68 | 1 |
| 9C | Corn Cob | Toluene | 144 | 5.4 | 5.3 | 167.0 | 67 | 1 |
| 10 | Corn Cob | Corn Oil | 75 | 20.4 | 3.5 | 170.3 | 51 | 5 |

| Example | Yields | | | | FF AQ/ORG | HMF AQ/ORG | FF:HMF MASS RATIO IN ORGANIC PHASE |
|---|---|---|---|---|---|---|---|
| | FF TOTAL [%] | HMF ORG [%] | HMF AQ [%] | HMF TOTAL [%] | | | |
| Comp A | 23 | 0 | 1 | 1 | — | — | — |
| Comp B | 61 | 21 | 2 | 23 | 0.02 | 0.1 | 2 |
| 1 | 72 | 3 | 3 | 6 | 0.03 | 1.3 | 24 |
| 2 | 67 | 1 | 2 | 3 | 0.03 | 1.4 | 42 |
| 3 | 69 | 2 | 5 | 7 | 0.03 | 1.9 | 25 |
| 4 | 62 | 0 | 2 | 2 | 0.29 | — | * |
| 5 | 66 | 1 | 2 | 4 | 0.03 | 1.7 | 27 |
| 6 | 72 | 1 | 5 | 7 | 0.03 | 4.1 | 29 |
| 7 | 57 | 0 | 2 | 2 | 0.03 | — | * |
| 8 | 91 | 0 | 2 | 2 | 0.02 | — | * |
| 9A | 68 | 4 | 4 | 8 | 0.01 | 1.0 | 16 |
| 9B | 69 | 5 | 8 | 13 | 0.01 | 1.6 | 12 |
| 9C | 68 | 4 | 6 | 10 | 0.01 | 1.6 | 15 |
| 10 | 56 | 1 | 1 | 2 | 0.10 | 1.3 | 43 |

In Table 3, FF ORG is yield of furfural based on the organic phase, while FF AQ is the furfural yield based on the aqueous phase and FF TOTAL is the cumulative furfural yield of the experiment.
HMF ORG is yield of furfural based on the organic phase, while HMF AQ is the furfural yield based on the aqueous phase and HMF TOTAL is the cumulative furfural yield of the experiment.
FF AQ/ORG is the ratio of FF in the aqueous and organic phases.
HMF AQ/ORG is the ratio of HMF in the aqueous and organic phases.
*As HMF was not detected in the organic phase, the mass ratio FF:HMF in the organic phase could not be calculated.

The data in Table 3 demonstrate that by starting from a lignocellulosic feedstock comprising both glucan and xylan and using a water-immiscible organic solvent of the Examples under the indicated reaction conditions, furfural can be obtained relatively free of HMF in the organic phase, despite the formation of HMF from the biomass. Furfural to HMF ratios on a weight basis are at least 12:1, or higher, in the Examples. In contrast, use of a non-selective organic solvent such as MIBK does not provide furfural in high selectivity in the organic phase, as shown by the FF:HMF mass ratio of 2:1 for Comparative Example B.

What is claimed is:

1. A process for the selective production of furfural, the process comprising the steps of:
    a) providing a lignocellulosic feedstock comprising glucan and xylan;
    b) contacting the feedstock with water in the presence of an acid catalyst to form a mixture;
    c) contacting the mixture formed in step b) with at least one water-immiscible organic solvent in a reactor and heating to a temperature from about 100° C. to about 220° C. to form a mixture comprising an aqueous phase and a furfural-containing organic phase,
        wherein the organic solvent and water are present in a weight ratio in the range of 7.7:1 to 32.1:1,
        wherein the organic phase further comprises 5-hydroxymethyl-2-furfural, and the weight ratio of furfural to 5-hydroxymethyl-2-furfural in the organic phase is at least 10:1 or higher, and
        wherein the water-immiscible organic solvent comprises at least one aliphatic hydrocarbon, cycloalkane, aromatic hydrocarbon, polyether containing ester or ether end groups, plant-derived oil, or mixtures thereof; and
    d) recovering furfural from the organic phase.

2. The process of claim 1, wherein step b) is performed prior to step c).

3. The process of claim 1, wherein steps b) and c) are performed concurrently.

4. The process of claim 1, wherein the acid catalyst comprises a mineral acid, a heteropolyacid, an organic acid, or a combination thereof.

5. The process of claim 4, wherein the acid catalyst is a mineral acid comprising sulfuric acid, phosphoric acid, hydrochloric acid, or a combination of these.

6. The process of claim 4, wherein the acid catalyst is a heteropolyacid comprising phosphotungstic acid, molybdophosphoric acid, or a combination of these.

7. The process of claim 4, wherein the acid catalyst is an organic acid comprising oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination of these.

8. The process of claim 1, wherein the at least one water-immiscible organic solvent is an aliphatic hydrocarbon comprising $CF_3CH_2CH_2CHF_2$, $CF_3CF_2CFHCFHCF_3$, $CF_3CF_2CHCl_2$, or mixtures thereof.

9. The process of claim 1, wherein the at least one water-immiscible organic solvent is a cycloalkane comprising cyclohexane, methylcyclohexane, or mixtures thereof.

10. The process of claim 1, wherein the at least one water-immiscible organic solvent is an aromatic hydrocarbon comprising benzene, toluene, a xylene, trifluorotoluene, or mixtures thereof.

11. The process of claim 1, wherein the at least one water-immiscible organic solvent is a polyether comprising polyethylene glycol containing ester or ether end groups, polypropylene glycol containing ester or ether end groups, or mixtures thereof.

12. The process of claim 1, wherein the at least one water-immiscible organic solvent is a plant-derived oil selected from the group consisting of corn oil, coconut oil, palm kernel oil, palm oil, soybean oil, and cottonseed oil, or mixtures thereof.

13. The process of claim 1, wherein the at least one water-immiscible organic solvent comprises toluene, trifluorotoluene, corn oil, or mixtures thereof.

14. The process of claim 1, wherein the step of recovering furfural is by distillation.

* * * * *